US012673151B2

(12) United States Patent
Bain

(10) Patent No.: US 12,673,151 B2
(45) Date of Patent: Jul. 7, 2026

(54) SYSTEM AND METHOD FOR TREATING FECAL IMPACTION

(71) Applicant: Growth Armor, LLC, Wilmington, DE (US)

(72) Inventor: Michael A. Bain, Costa Mesa, CA (US)

(73) Assignee: Growth Armor, LLC, Wilmington, DE (US)

( * ) Notice: Subject to any disclaimer, the term of this patent is extended or adjusted under 35 U.S.C. 154(b) by 354 days.

(21) Appl. No.: 18/297,428

(22) Filed: Apr. 7, 2023

(65) Prior Publication Data

US 2024/0335602 A1 Oct. 10, 2024

(51) Int. Cl.
*A61M 3/02* (2006.01)

(52) U.S. Cl.
CPC ..... *A61M 3/0275* (2013.01); *A61M 2202/068* (2013.01)

(58) Field of Classification Search
CPC ................ A61M 3/0258; A61M 1/772; A61M 2250/00; A61M 3/02; A61M 3/0202; A61M 3/0287
USPC ... 604/357, 375, 37, 276, 328, 28, 319, 322, 604/514, 540, 317, 99.02, 118, 119, 30, 604/318, 323, 326, 334, 335, 35, 36, 48; 600/156
See application file for complete search history.

(56) References Cited

U.S. PATENT DOCUMENTS 4,190,059 A * 2/1980 Holt ...................... A61M 3/025 604/27
4,716,748 A 1/1988 Watanuki et al.
5,019,056 A * 5/1991 Lee ...................... A61M 3/0258 604/257
8,545,480 B2 10/2013 Tan
10,765,796 B2 * 9/2020 Foley .................... A61M 3/022
2003/0195481 A1 * 10/2003 Xu ........................ A61M 31/00 604/275
2006/0173244 A1 * 8/2006 Boulais .................. A61B 1/015 600/156
2012/0029485 A1 * 2/2012 Tan ...................... A61M 3/0287 604/540
2019/0247566 A1 * 8/2019 Hassidov ................ A61M 1/73
2022/0054733 A1 * 2/2022 Hassidov ............ A61M 3/0202
2022/0379001 A1 12/2022 Sharma et al.

OTHER PUBLICATIONS

PCT Search Report for PCT/US2024/021757; Jul. 10, 2024.

* cited by examiner

*Primary Examiner* — Michele Kidwell
(74) *Attorney, Agent, or Firm* — Stetina Garred Brucker & Newboles

(57) ABSTRACT

Systems and methods for irrigation devices for treatment of fecal impaction in a patient are contemplated. An irrigation device may comprise a distal portion comprising a disimpaction fluid inlet and a waste vacuum outlet. The disimpaction fluid outlet may be operative to emit a generally annular jet of disimpaction fluid into the anus of the patient so as to disimpact impacted feces associated with the anus. The irrigation device may additionally comprise a waste vacuum inlet configured to receive and remove the disimpacted feces. When the distal portion is placed at and aligned with the anus of a patient, the emitted disimpaction fluid may disimpact feces so that the disimpacted feces may be safely received by the waste vacuum inlet to be safely isolated from the surrounding environment.

17 Claims, 4 Drawing Sheets

116

SYSTEM AND METHOD FOR TREATING FECAL IMPACTION

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Field of Invention

The present invention relates to systems and methods for treating fecal impaction of a patient. More specifically, the present application relates to a hand-held device for treating fecal impaction via vigorous fluid disimpaction methods.

2. Related Art

In human digestive systems, food is digested via the gastrointestinal tract typically through the mouth, esophagus, stomach, small intestine, and large intestine in that order. Throughout the gastrointestinal tract, several species such as nutrients and water are absorbed from the food and distributed to different cells across the body. Not all of the species carried by food are digested, and as such the leftover material, which may be referred to as fecal matter, feces, or stool, will move through the colon and into the rectum, where it may be stored before being ejected from the anus.

The gastrointestinal system may suffer from various conditions leading to fecal incontinence or fecal impaction, with one of the most common conditions being constipation. As stool travels through the colon, water is absorbed from the stool to convert it from a liquid form to a soft, smooth solid that is easy to eject from the anus. Constipation arises when too much water is absorbed from the stool, which causes the stool to become hard, rough, and dry in a form that is much more difficult to eject from the anus. Constipation may be caused by a number of factors, with the most common cases arising when the colon absorbs too much water from the stool due to the stool remaining in the colon for too long, since there is no strong control mechanism to stop this water absorbing mechanism from happening as the stool remains in the colon.

Constipation can give way to medical diagnoses such as IBS-C (Irritable Bowel Syndrome with Constipation) and CIC (Chronic Idiopathic Constipation) which may cost patients and hospitals thousands of dollars to treat properly, especially since treating these conditions tends to have a high rate of treatment failure.

People who regularly suffer from constipation or other forms of fecal impaction are generally advised to make lifestyle changes to prevent the condition, such as increasing exercise and fiber intake, but for more serious cases of chronic constipation, one may need to turn to more direct treatment methods. There are several types of medication that treat bowl movement which are generally referred to as laxatives. These include fiber supplements, lubricants, and stimulants. There are additionally stronger medications that can be prescribed to treat chronic constipation, such as lubiprostone (Amitiza®), linaclotide (Linzess®), and plecanatide (Trulance®) to name a few. The cost of using these medications can add up significantly over time to a consumer who has chronic constipation issues.

In addition to these treatments, there are devices that can be used to provide a impaction treatment methodology. Most of these devices apply pressure in one form or another so as to stimulate bowel movement or to otherwise mechanically disimpact the impacted feces. For example, some devices aim to replicate massage techniques used by therapists to loosen certain muscles in the colon and rectum. Others apply a kneading-like motion on the abdomen to give a similar effect. These types of devices can suffer from the drawback of being confusing and convoluted for someone to operate and/or inconvenient for the user to set up. Additionally, these devices can cause other forms of discomfort from applying pressure to parts of the anus or rectum and making them sore, causing undue harm to the patient or user.

Other devices look to solve this issue by applying or injecting water around or into the anus to soften up the hard stool inside, generally known as irrigation. These can include enemas to modified spray bottles. These devices, however, can give less than desirable results given that specialized treatment cannot be reliably given and may additionally be challenging for someone to use by themselves alone and in private.

Many of these techniques and methods don't have a way of addressing the safe collection and isolation of feces that become disimpacted from the anus. More severe cases of fecal impaction may require one to lay on their back to treat properly, and it can be challenging to prevent the dislodged stool from contaminating the surrounding environment in this type of orientation.

It is therefore desirable to develop improved devices for relieving constipation that allow for case of use and effective results, which combine irrigation and manual disimpaction techniques. It is also desirable to develop improved devices for relieving constipation that can be used for at home and hospital use without causing too much discomfort to the user suffering from fecal impaction.

BRIEF SUMMARY

To solve these and other problems, irrigation devices are contemplated in which one or more outlet apertures of the irrigation device may be configured to emit a jet of disimpaction fluid into the anus of a patient to both irrigate and mechanically disimpact impacted feces. The disimpacted feces may then be removed via a waste vacuum inlet of the irrigation device, which itself may be fluidly connected to a source of vacuum operative to suck in the disimpacted feces. The irrigation device may be handheld and configured for a patient or user to utilize privately at home, or the irrigation device may be configured for use in a medical facility such as a hospital such that it may connect to different medical devices that may be found there.

An irrigation device contemplated herein may comprise: a body portion comprising a disimpaction fluid inlet and a waste vacuum outlet and a distal portion configured for placement at and alignment with the anus of a patient. The distal portion may comprise a disimpaction fluid outlet and a waste vacuum inlet. The disimpaction fluid outlet may comprise one or more outlet apertures arranged to define an annulus, with each outlet aperture being configured to emit a jet of disimpaction fluid. The waste vacuum inlet may comprise one or more inlet apertures positioned internal to the annulus defined by the disimpaction fluid outlet, with the disimpaction fluid inlet being configured to fluidly connect to a disimpaction fluid reservoir for receiving a supply of disimpaction fluid. The waste vacuum outlet may be configured to fluidly connect to a waste vacuum reservoir for supplying a source of vacuum and for receiving waste. When the irrigation devices is fluidly connected to a disimpaction fluid reservoir and is fluidly connected to a waste vacuum reservoir, and when the distal portion is placed at and aligned with the anus of a patient, the disimpaction fluid outlet may be operative to emit a generally annular jet of disimpaction fluid into the anus of the patient so as to disimpact impacted feces. The waste vacuum inlet may be configured to receive and remove disimpacted feces.

The irrigation device may have the body portion sized and configured to be manually held in the hand of an operator when in operation.

The disimpaction fluid used may be selected from the group consisting of: water, an intravenous fluid, a crystalloid solution, a colloidal solution, a buffer solution, a gas, or combinations thereof.

The disimpaction fluid outlet of the irrigation device may comprise a plurality of individual outlet apertures arranged in an annular configuration, the plurality of individual outlet apertures being configured to collectively emit a generally annular jet of disimpaction fluid. In another embodiment, the disimpaction fluid outlet of the irrigation device may comprise a single annular outlet aperture configured to emit a generally annular jet of disimpaction fluid.

In some embodiments, the disimpaction fluid outlet may be configured to emit heated disimpassion fluid via the body portion further comprising a heating element for heating disimpaction fluid supplied by a disimpaction fluid reservoir. In an alternative embodiment, the disimpaction fluid outlet may be configured to emit heated disimpassion fluid via the body portion being configured to receive disimpaction fluid that is heated prior to the disimpaction fluid being received at the disimpaction fluid inlet.

The body portion of the irrigation device may further comprise one or more pumps for pumping disimpaction fluid through one or more conduits within the body portion.

The irrigation device may be configurable to enable the disimpaction fluid outlet to emit a generally annular jet of disimpaction fluid according to one or more predefined jet configurations. These one or more predefined jet configurations may comprise the selection of a value for at least one adjustable parameter, the at least one adjustable parameter being selected from: disimpaction fluid velocity, disimpaction fluid flow rate, disimpaction fluid temperature, disimpaction fluid jet cone angle, or combinations thereof.

A method for treating fecal impaction in a patient is also contemplated. The method may comprise the steps of providing an irrigation device comprising a body portion, the body portion comprising a disimpaction fluid inlet and a waste vacuum outlet, and a distal portion configured for placement at and alignment with the anus of a patient, the distal portion comprising a disimpaction fluid outlet and a waste vacuum inlet, the disimpaction fluid outlet comprising one or more outlet apertures arranged to define an annulus, each outlet aperture being configured to emit a jet of disimpaction fluid, the waste vacuum inlet comprising one or more inlet apertures positioned internal to the annulus defined by the disimpaction fluid outlet, fluidly connecting the disimpaction fluid inlet to a disimpaction fluid reservoir for receiving a supply of disimpaction fluid, fluidly connecting the waste vacuum outlet to a waste vacuum reservoir for supplying a source of vacuum and for receiving waste, and placing the distal portion at and in alignment with the anus of a patient, and actuating the irrigation device in order to cause the disimpaction fluid outlet to emit a generally annular jet of disimpaction fluid into the anus of the patient so as to disimpact impacted feces, with the disimpacted feces being received by and removed from the patient via the waste vacuum inlet.

The body portion of the provided irrigation device may be sized and configured to be manually held in the hand of an operator when in operation.

The disimpaction fluid used may be selected from the group consisting of: water, an intravenous fluid, a crystalloid solution, a colloidal solution, a buffer solution, a gas, or combinations thereof.

The disimpaction fluid outlet may comprise a plurality of individual outlet apertures arranged in an annular configuration, the plurality of individual outlet apertures being configured to collectively emit a generally annular jet of disimpaction fluid. The disimpaction fluid outlet may alternatively comprise a single annular outlet aperture configured to emit a generally annular jet of disimpaction fluid.

The disimpaction fluid outlet may be configured to emit heated disimpassion fluid via the body portion further comprising a heating element for heating disimpaction fluid supplied by a disimpaction fluid reservoir. The disimpaction fluid outlet may also or alternatively be configured to emit heated disimpassion fluid via the body portion being configured to receive disimpaction fluid that is heated prior to the disimpaction fluid being received at the disimpaction fluid inlet.

The body portion of the irrigation device of these methods may further comprise one or more pumps for pumping disimpaction fluid through one or more conduits within the body portion.

The irrigation device of these methods may be configurable to enable the disimpaction fluid outlet to emit a generally annular jet of disimpaction fluid according to one or more predefined jet configurations. These one or more predefined jet configurations may comprise the selection of a value for at least one adjustable parameter, the at least one adjustable parameter being selected from: disimpaction fluid velocity, disimpaction fluid flow rate, disimpaction fluid temperature, disimpaction fluid jet cone angle, or combinations thereof.

Each of the herein disclosed embodiments are contemplated to be within the scope of the invention herein disclosed. These and other embodiments will become readily apparent to those skilled in the art form the following detailed description of the preferred embodiments having reference to the attached figures, the invention not being limited to any particular preferred embodiments disclosed.

BRIEF DESCRIPTION OF THE DRAWINGS

These and other features and advantages of the various embodiments disclosed herein will be better understood with respect to the following description and drawings, in which like numbers refer to like parts throughout, and in which.

Common reference numerals are used throughout the drawings and the detailed description to indicate the same elements.

DETAILED DESCRIPTION

Figure 1:
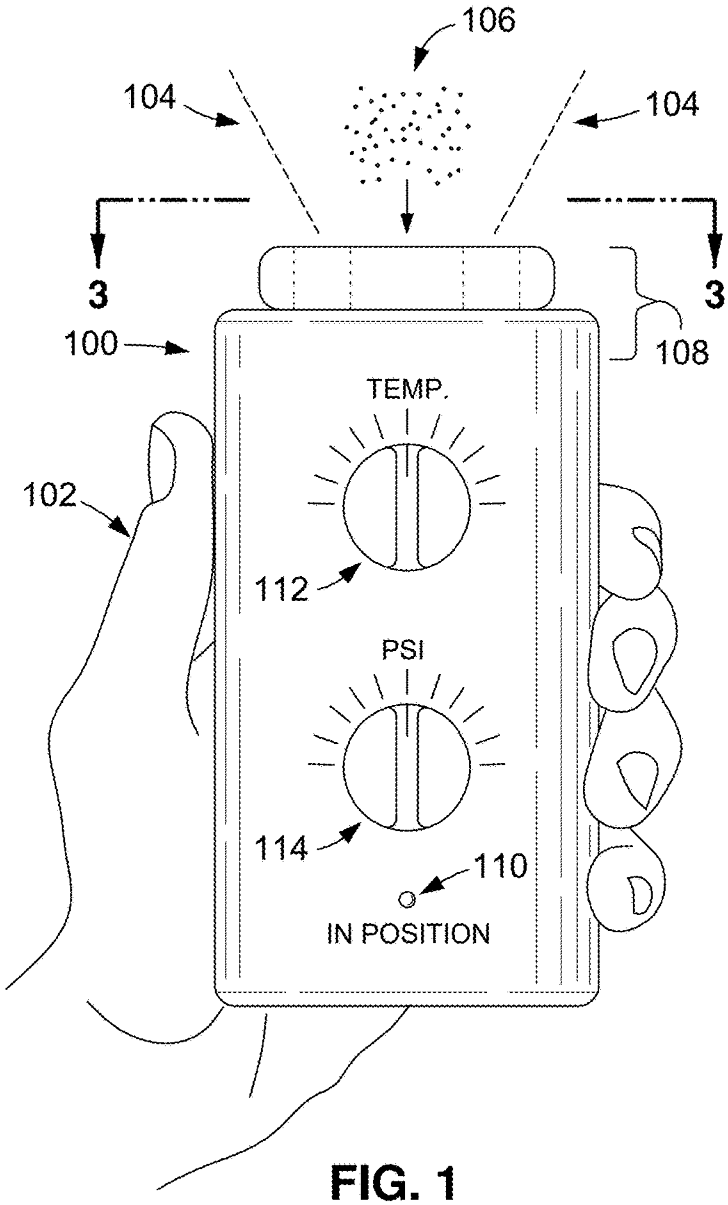
FIG. 1 is a front elevational view of a first embodiment of the irrigation device.

According to various aspects of the present disclosure, an irrigation and manual disimpaction device for treatment of fecal impaction in a patient are contemplated. The device may comprise a body portion that itself comprises a disimpaction fluid inlet and a waste vacuum outlet. Once a distal portion of the irrigation device is placed at and aligned with the anus of a patient, a disimpaction fluid may be emitted from a disimpaction fluid outlet of the irrigation device to disimpact impacted feces. The disimpacted feces may be received and safely removed and isolated via a waste vacuum inlet. This irrigation device allows for effective removal of feces that can be collected with minimal contamination of the surrounding environment.

The irrigation device may be configured for use at the home of a user or at a medical facility such as a hospital. For example, if used at home the body portion of the irrigation device may be sized and configured to manually be held in the hand of a user.

The disimpaction fluid inlet of the irrigation device may be fluidly connected to a disimpaction fluid reservoir that may receive a supply of disimpaction fluid. As such, it can be seen that the irrigation device may be completely separate from a disimpaction fluid reservoir. Alternatively, the disimpaction fluid reservoir may be built into the irrigation device and thus a structural part of the irrigation device. When the disimpaction fluid inlet and a disimpaction fluid reservoir are fluidly connected, a disimpaction fluid outlet with one or more outlet apertures on the distal end portion of the device may be configured to emit a jet of disimpaction fluid through each of the one or more outlet apertures. This may allow a generally annular jet of disimpaction fluid to be emitted from the disimpaction fluid outlet. This generally annular jet of disimpaction fluid may target feces associated with the anus of the user or patient the irrigation device is operating upon. This targeting may be operative to disimpact impacted feces, irrigate the feces and/or the anus, soften the feces, neutralize the feces, break up the feces, or combinations thereof. The feces may be disimpacted or otherwise treated via the generally annular jet of disimpaction fluid being emitted directly onto the feces or onto regions of the anus associated with the impacted feces to be disimpacted.

The generally annular jet of disimpaction fluid may be according to one or more predefined jet configurations, these configurations comprising the selection of at least one adjustable parameter including disimpaction fluid velocity, disimpaction fluid flow rate, disimpaction fluid temperature, disimpaction fluid jet cone angle, or combinations thereof. A user/patient/operator utilizing the irrigation device may adjust these parameters and/or change the predefined jet configuration of the device directly. This may be via a mechanism on the device (ex. twisting part of the device, pushing a button on the device, etc.) or via a communication with a control unit on the device which may change the parameters and/or the configurations (ex. a user using an application on their phone to set parameters/configurations and the device adjusting in response to this information). It can be seen that certain selections of parameters/configurations may be better suited to particular patients/users the device may be operated upon, and as such this irrigation device may disimpact or otherwise treat feces much more effectively than other prior art methods by administering a treatment methodology that is catered specific for a particular user/patient.

It can therefore be seen that the emitted generally annular jet of disimpaction fluid may have various fluid properties which may help to disimpact the impact feces. For example, a forceful and turbulent flow of disimpaction fluid may be more effective at rupturing and breaking up feces. The outlet apertures may be sized and configured so that the disimpaction fluid may have a Venturi effect which may be more effective at targeting particular areas of the anus.

The irrigation device may comprise a controller operative to change or modify the adjustable parameters over a period of time as desired by the user/patient/operator. For example, the disimpaction fluid velocity and/or the disimpaction fluid flow rate may be steadily increased until it overcomes an anal sphincter pressure.

The vacuum outlet of the irrigation device may be fluidly connected to waste vacuum reservoir that may supply a source of vacuum and for receiving waste. As such, it can be seen that the waste vacuum reservoir may be completely separate from a waste vacuum reservoir. Alternatively, the waste vacuum reservoir may be built into the irrigation device, which may further make the waste vacuum reservoir a structural part of the irrigation device. When the waste vacuum outlet and a waste vacuum reservoir are fluidly connected, the waste vacuum reservoir may be able to receive disimpacted feces and supply a source of vacuum. A waste vacuum inlet of the distal portion of the device that may comprise one or more inlet apertures may receive recently disimpacted feces. The source of vacuum may then induce the feces to be sucked into, fall into, or otherwise be received by the one or more inlet apertures and into a waste vacuum reservoir where they may be safely isolated from the user, patient, and/or operator and the surrounding environment. The disimpacted feces may then be properly disposed of or treated from a waste vacuum reservoir.

The device may incorporate one or more macerators operative to macerate or otherwise break up the disimpacted feces. The disimpacted feces may be broken up by a macerator soon after being received by the one or more inlet apertures. The disimpacted feces may also be broken up by the maceratoras they reach a certain volume or mass threshold in the waste vacuum reservoir. The macerator may be positioned anywhere along the pathway in which the disimpacted feces travel through or wherever the disimpacted feces may accumulate. The macerator may be operative to actuate when the device is operated, or the macerator may simply turn on and off when a user/patient/operator activates a switch specific to the macerator or some device in communication with a control unit controlling the operation of the macerator. It can be seen that a macerator may be similar in form and operation to macerator units that are incorporated into many conventional waste processing systems. Larger chunks of disimpacted feces may be more challenging to store in the waste vacuum reservoir since they can take up a large volume of the waste vacuum reservoir while leaving lots of wasted void spaces in the waste vacuum reservoir unoccupied by any of the received disimpacted feces. As such, the macerator may assist in chopping up and breaking down the disimpacted feces so that more of the volume of waste vacuum reservoir may be utilized in receiving disimpacted feces.

The disimpaction fluid may be any fluid which is operative to disimpact or otherwise treat impacted feces associated with the patient or user's anus. Examples include water, crystalloid solutions, colloidal solutions, buffer solutions, gases, or combinations thereof. An operator using the irrigation device may understand which types of fluids may be better suited to treat certain types of fecal impaction or constipation, and as such the selection of disimpaction fluid may be selected so as to achieve the best results for a particular application.

The irrigation device may be further configured to undergo a cleaning procedure to clean the device. As disimpacted feces are being received by the waste vacuum inlet, feces may stain parts of the irrigation device and/or residue from the feces may accumulate on parts of the irrigation device. In order to ensure that the device can be reused without health risks that may be associated with doing so, a cleaning procedure may be activated in which the disimpaction fluid may be emitted onto portions of the device, including but not limited to areas in and around the waste vacuum inlet and disimpaction fluid outlet. Similar to switching between the adjustable parameters and predefined configurations above, this cleaning procedure may be activated via a mechanism on the device or an external communication with the irrigation device.

Turning now to FIG. 1, an elevation view of a first exemplary embodiment of an irrigation device is shown. The irrigation device 100 can be sized to fit in the hand 102 of a user. This small and easy to grip form factor allows for the irrigation device 100 to be positioned and aimed by the user with ease for at home use. Jets of disimpaction fluid 104 are emitted by outlet apertures 116 away from the distal portion 108 and towards the anus of a patient/user. The jet configuration may be configured, such as illustrated this figure, such that the jet or jets of disimpaction fluid 104 diverge when emitted. As such, the disimpaction fluid 104 in the configuration depicted in this embodiment may, for example, be targeting multiple distinct impacted feces, a singular impacted feces, or regions of the anus that the impacted feces may be attached to. Disimpacted feces 106 may be received by the waste vacuum inlet and through the inlet aperture 118.

The distal portion 108 of the device may comprise of a soft material, a built-in lubricant, and/or pressure sensors. The soft material could be a rubberized or fabric material that would not cause an adverse reaction when placed against the anus of a patient/user. The built-in lubricant may also give similar results. A benefit of the disclosed irrigation devices over prior art methods is that these devices need not be pushed up against with force or otherwise forced into the anus of a patient/user in order to operate effectively in disimpacting and removing feces.

In preferred embodiments and methods, the device 100 may be aligned and positioned against the anus without excessive force. When a particular pressure reading is reached on a certain portion of the pressure sensors, the user may be notified by an LED light 110 labeled "IN POSITION" that may turn on when that condition is reached. The irrigation device 100 may also have an audio notification or be notified by an external device in communication with the irrigation device 100 to let the user/patient/operator know that the device 100 is properly placed at and aligned with the anus of a patient.

The user may modify the adjustable parameters of the disimpaction fluid 104 being emitted from the outlet apertures 116 by operating knobs that may be on the irrigation device 100. The temperature knob 112 may control the operation of a heating element 130 which itself is operative to heat the fluid 104 to the temperature set by the knob. Similarly, the pressure knob 114 may control the operation of one or more pumps 128 such that the disimpaction fluid 104 may be emitted at the disimpaction fluid velocity or disimpaction fluid flow rate set by the knob.

It may be appreciated that the first embodiment of the irrigation device 100 may be used by a user in the private comfort of their home with case. The device 100 can be turned on or off simply and used quickly with little preparation needed on the user's part, and the device 100 may be small and easy to grip allowing for minimal difficulty for a user in aiming and positioning it.

Figure 2:
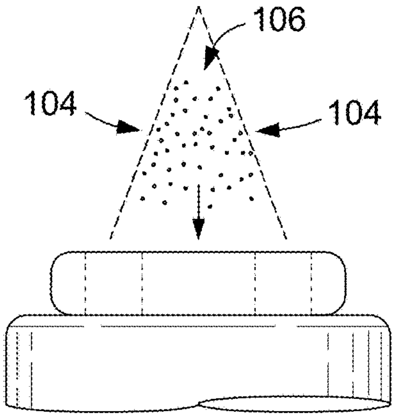
FIG. 2 is close up view of part of the distal portion of the first embodiment of the irrigation device operated in an alternative jet configuration.

Turning now to FIG. 2, a close-up view of part of the distal portion of the first exemplary embodiment of the irrigation device operated in an alternative jet configuration is shown. The disimpaction fluid 104 in this figure has been set to an alternative jet configuration such that the emitted disimpaction fluid 104 converges to a singular point. In this configuration, the disimpaction fluid 104 may, for example, be targeted towards a particular impacted feces or a specific region of or within the anus. This alteration of the jet configuration can be performed by a number of different methods, including but not limited to those disclosed herein. The irrigation device 100 may also be operative to be set to automatically transition between different jet configurations while the device is in operation. An example of this may be cycling between the configurations shown in FIG. 1 and FIG. 2 every 30 seconds. An operator operating the irrigation device 100 on a patient may also be able to manually switch between different jet configurations to target particular feces or areas of the anus as the operation is proceeding. This adjustable and adaptable treatment methodology allows for efficient and effective disimpaction treatment of impacted feces that can be tailored to individuals with differing levels or types of fecal impaction/constipation.

Figure 3:
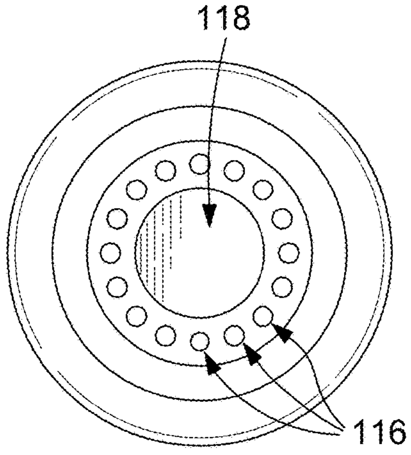
FIG. 3 is a top plan view of the first embodiment of the irrigation device.

Bringing our attention now to FIG. 3 a top schematic view of a first exemplary embodiment of the irrigation device is depicted. Here, the disimpaction fluid outlet comprises a plurality of individual outlet apertures 116 which may be configured to collectively emit a generally annular jet of disimpaction fluid. The waste vacuum inlet may receive and remove the disimpacted feces 106. The disimpacted feces may go through one of the inlet apertures 118. According to one particular embodiment of the irrigation device contemplated herein, these outlet apertures 116 are arranged to define an annulus, with one or more inlet apertures 118 positioned internal to this annulus. The jet configurations and the adjustable parameters may be set such that the disimpaction fluid 104 may guide the disimpacted feces 106 towards the one or more inlet apertures 118, wherein the vacuum source may suck in the disimpacted feces safely away from the user/patient/operator and the surrounding environment and into a waste vacuum reservoir. It may also be seen that the spacing, size, and number of the outlet apertures 116 and the inlet apertures 118 may be configured in several different ways, examples of such configurations which are depicted in further figures. Specifically, in FIG. 3 it may be seen that there are sixteen outlet apertures 116 and a single inlet aperture 118, but in other embodiments, it may be seen that there may be more or less outlet apertures 116 and additional inlet apertures 118.

Figure 4:
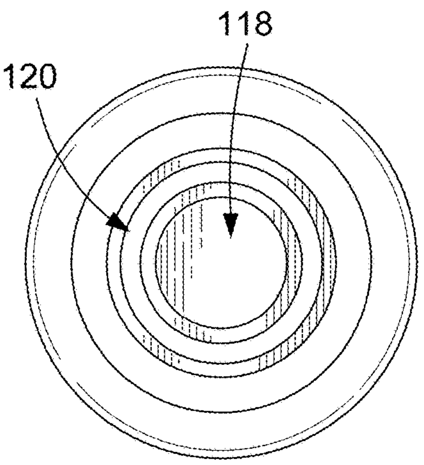
FIG. 4 is a top plan view of a second embodiment of the irrigation device.

Turning our attention now to FIG. 4, a top schematic view of a second embodiment of the irrigation device is shown. In this embodiment, the disimpaction fluid outlet may be seen to comprise a single annular outlet aperture 120. It may be appreciated that this arrangement is in contrast to the previous embodiment shown in FIG. 3, has several distinct outlet apertures 116. IKt may thus be seen that the singular annular outlet aperture 120 may emit a generally continuous jet of disimpaction fluid 104, in a generally annular jet configuration.

Figure 5:
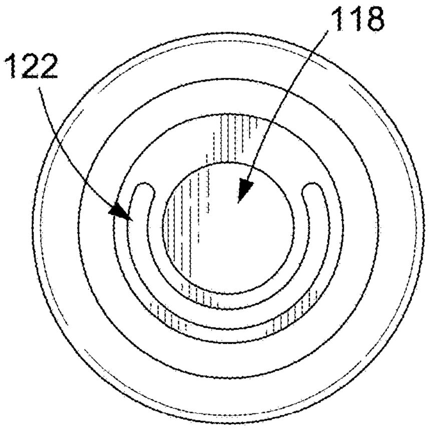
FIG. 5 is a top plan view of a third embodiment of the irrigation device.

Turning now to FIG. 5, a top schematic view of a third embodiment of the irrigation device is depicted. This particular embodiment may be seen to be generally similar to the previous embodiment of FIG. 4, except that the outlet aperture 122 is not continuous along its annular configuration. As such, the outlet aperture 122 may still be seen to define an annulus in which the one or more inlet apertures 118 are positioned internal to, even if the outlet aperture 122 may not itself fully extend in a continuous, unbroken fashion around the entirety of the annular region. The rest of the annulus that the partial outlet aperture may simply be a smooth surface which may comprise the aforementioned soft material, built-in lubricant, and/or pressure sensor(s). In particular, it may be seen that this particular embodiment may be beneficial if a particular user/patient has constipation/fecal impaction associated with a particular region or area, which this embodiment may be more suited to treat directly.

The irrigation device 100 may also be configured such that the disimpaction fluid outlet of a particular irrigation device may be changed from one embodiment to another. Such reconfiguration may be as simple as a user/patient/operator twisting off or otherwise detaching a part of the irrigation device 100 and attaching a new part in place of the detached part. As such, it may be possible to have a singular irrigation device 100 and be able to switch between having a plurality of outlet apertures 116, a single outlet aperture 120, or a partial outlet aperture 122, or other configurations of outlet and inlet apertures, according to the particular needs of the patient.

Figure 6:
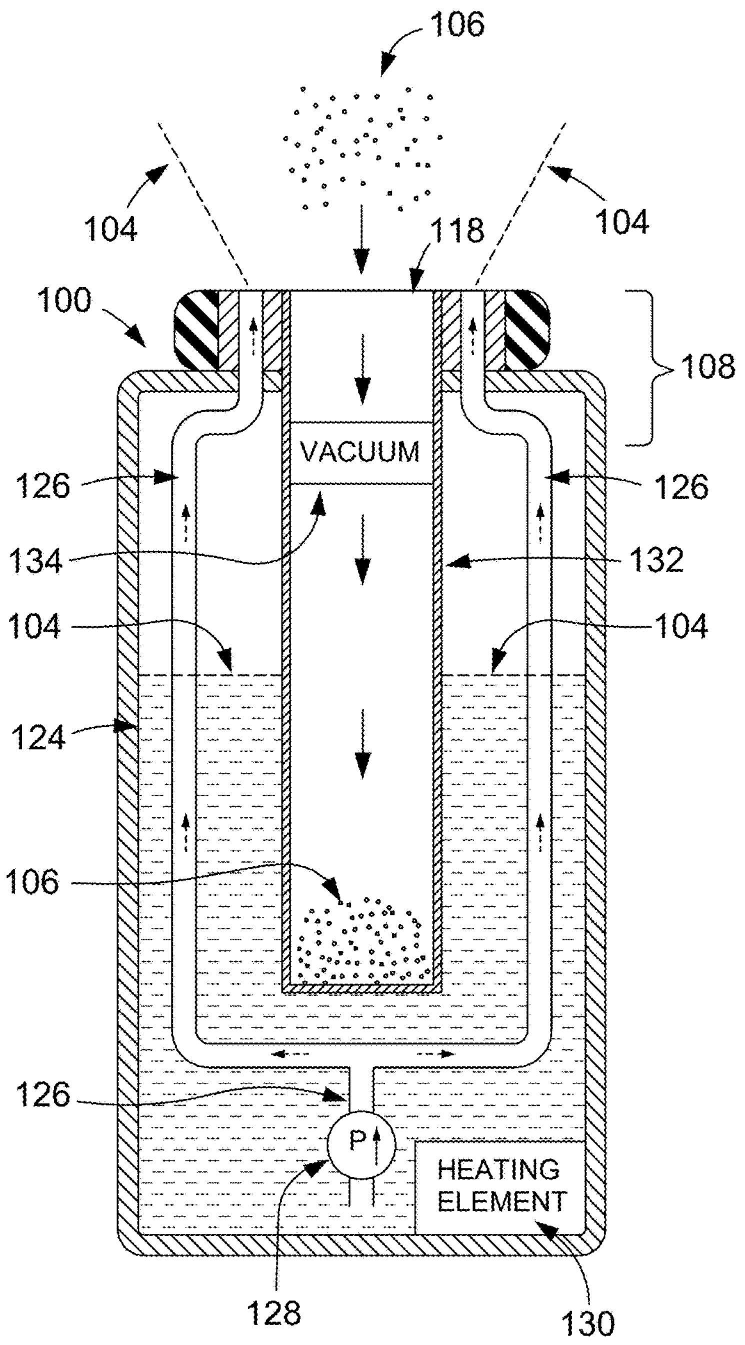
FIG. 6 is a front elevational cross-sectional view of the first embodiment of the irrigation device.

Turning now to FIG. 6, a front elevational cross-sectional view of the first exemplary embodiment of the irrigation device is shown. Here, it may be seen that a disimpaction fluid reservoir 124 with a supply of disimpaction fluid 104 is fluidly connectable to the disimpaction fluid inlet and the disimpaction fluid outlet of the device 100 via fluid conduits 126. The body portion of the irrigation device 100 may comprise one or more pumps 128 which may pump the disimpaction fluid through the fluid conduits 126. The device 100 depicted here a single fluid conduit 126 which then diverges into two fluid conduits 126, but in other embodiments the fluid conduits 126 may diverge, or there may be multiple fluid conduits 126 that converge or diverge, or there may just be a single fluid conduit 126 that does not diverge nor converge. It may be seen that the pumps 128 may serve to pump the disimpaction fluid to transport it from the disimpaction fluid reservoir 124, then to the disimpaction fluid inlet, followed by the disimpaction fluid outlet where the outlet apertures 116 may emit the disimpaction fluid 104 towards the anus of a patient/user. The operation of the pump 128 may also adapt in response to a change in the aforesaid adjustable parameters, which may cause the pump 128 to change, for example, the disimpaction fluid velocity and/or the disimpaction fluid flow rate. The disimpaction fluid reservoir 124 may be operative to receive a supply of disimpaction fluid 104 via, for example, a port on the device 100 which may allow a user/patient/operator to fill or empty the disimpaction fluid reservoir 124 with a supply of disimpaction fluid 104. The device 100 and the disimpaction fluid reservoir 124 may also be configured such that the device 100 and the disimpaction fluid reservoir 124 may be detached from each other and subsequently reattached from each other as desired.

The body portion of the irrigation device 100 may also comprise a heating element 130. This heating element 130 may heat the disimpaction fluid 104 supplied by the disimpaction fluid reservoir 124. The operation of the heating element 130 and the temperature at which the heating element 130 heats the disimpaction fluid 104 to may change, for example, in response to someone changing the temperature knob 112 to a particular temperature reading. The temperature of the disimpaction fluid 104 may change how effective the disimpaction fluid 104 may disimpact or otherwise treat impacted feces of the patient/user and/or the patient/user's reaction to the fluid (for it might be less agitating for a user/patient to have a warm disimpaction fluid 104 emitted towards the anus as opposed to an extremely hot or cold disimpaction fluid 104).

The irrigation device may also have a waste vacuum outlet fluidly connected to a waste vacuum reservoir 132. The waste vacuum reservoir 132 may have a source of vacuum 134 which may aid in guiding the disimpacted feces 106 through the one or more inlet apertures 118 of the waste vacuum inlet and into the waste vacuum reservoir 132. The source of vacuum 134 may be turned on or off by a user/patient/operator using the device 100, and it may be set to operate when the disimpaction fluid 104 is being emitted from the one or more outlet apertures 120. As the device 100 is being used and the waste vacuum reservoir 132 is receiving disimpacted feces 106, the user/patient/operator may be notified when the waste vacuum reservoir 132 approaches full capacity, resulting when enough disimpacted feces 106 have accumulated therein. This can be via an LED light similar to the "IN POSITION" LED light 110 or an audio notifier, to name a couple of examples. The previously mentioned macerator that may break up the disimpacted feces 106 is not present in this figure, but if one or more macerators are present they may be found in the waste vacuum reservoir 132 anywhere along the pathway the disimpacted feces 106 follow or at the site where they accumulate at the bottom of the waste vacuum reservoir. Similar to the disimpaction fluid reservoir 124, the waste vacuum reservoir 132 and the irrigation device 100 may be configured such that the waste vacuum reservoir 132 and the device 100 may be detached from each other and subsequently reattached from each other as desired. This may allow one to detach the waste vacuum reservoir 132 from the irrigation device 100 when the waste vacuum reservoir 132 starts to become full of disimpacted feces 106. The disimpacted feces 106 that have collected in the waste vacuum reservoir 132 may then be emptied or otherwise disposed of properly. The waste vacuum reservoir 132 may then be cleaned before being reattached and reused in the irrigation device 100.

Figure 7:
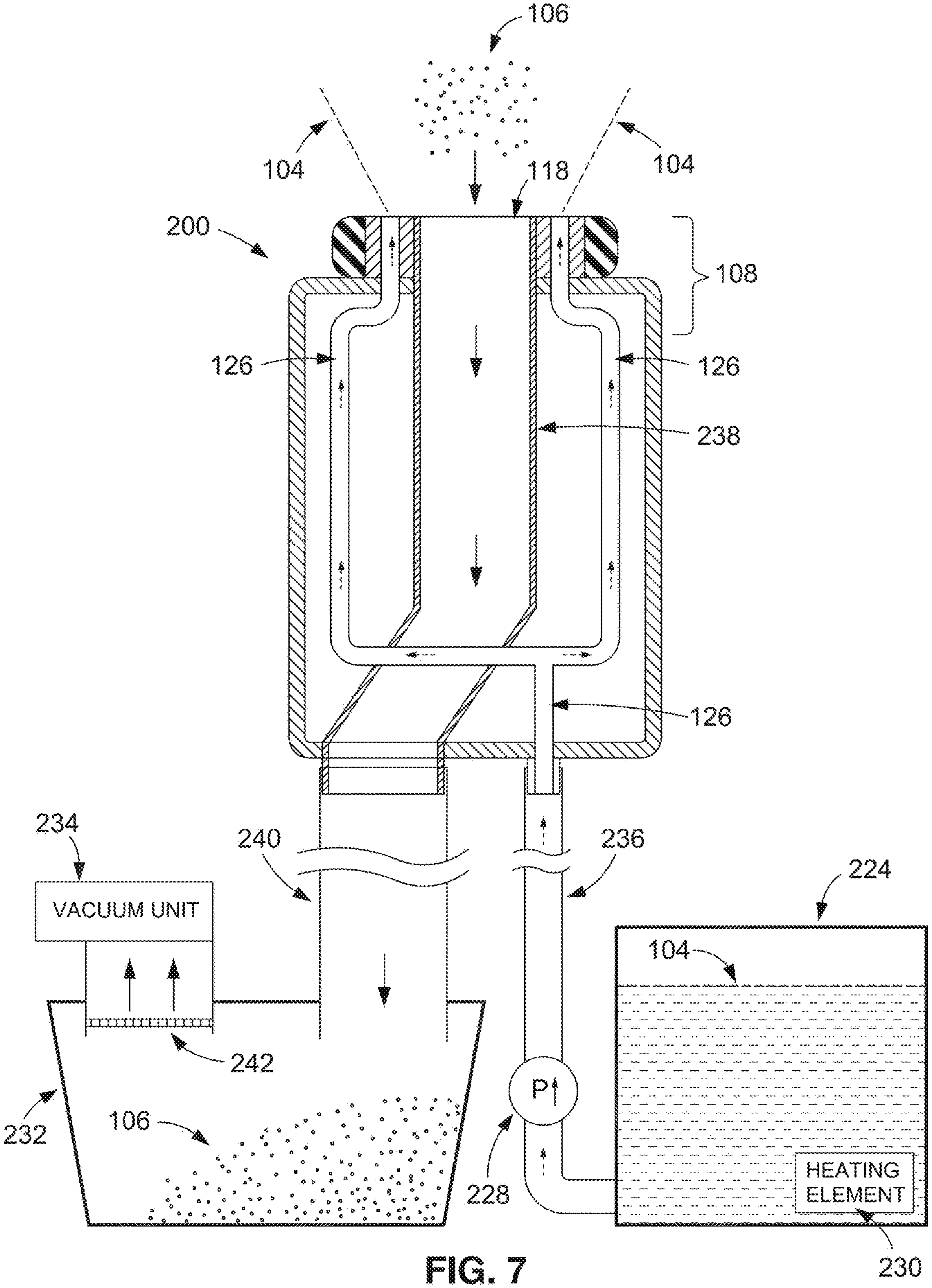
FIG. 7 is a front elevational view of a cross-sectional view of a fourth embodiment of the irrigation device attached to modular units.

Turning now to FIG. 7, a front elevational view of a cross-sectional view of a fourth exemplary embodiment of the irrigation device attached to modular units is shown. This embodiment of an irrigation device 200 depicted may include a number of similar features as in the previously discussed exemplary embodiments of irrigation devices 100, such as fluid conduits 126, a single inlet aperture 118, outlet apertures 116 and the collection of disimpacted feces 106. This irrigation device 200 may further still be seen to have disimpaction fluid reservoir 224 fluidly connected to the disimpaction fluid inlet of the device 200 and a waste vacuum reservoir 232 fluidly connected to the waste vacuum outlet of the device 200, except that in this particular embodiment both of the reservoirs 224, 232 are outside of the body portion of the device 200.

The disimpaction fluid reservoir 232 may hold a larger volume of disimpaction fluid 104 in this embodiment when compared to the previous device 100. This disimpaction fluid reservoir 224 may comprises a heating element 230 which may heat the disimpaction fluid 104 to a desired temperature. As such, the body portion of the device 200 may be operative to receive this disimpaction fluid 104 that is heated prior to being received at the disimpaction fluid inlet of the device 200. The irrigation device 200 may additionally have a pump 228 which may pump the disimpaction fluid 104 from the disimpaction fluid reservoir 224 through external fluid conduits 236 and through the fluid conduits 126 such that the disimpaction fluid 104 may travel through the disimpaction fluid inlet and the disimpaction fluid outlet and subsequently emitted towards the anus.

The waste vacuum reservoir 232 may also have a larger volume to hold more disimpacted feces 106 that is received by the waste vacuum inlet. The disimpacted feces may thus travel through a waste conduit 238 in the body portion of the device 200 and through an external waste conduit 240 so that the disimpacted feces 106 may be received by the waste vacuum reservoir 232. It can be seen that the waste vacuum reservoir 232 is connected to a source of vacuum 234, with the source of vacuum 234 being operative to suck in and guide disimpacted feces 106 to the waste vacuum reservoir 232. The waste vacuum reservoir 232 has a filter 242 to prevent the disimpacted feces 106 from being sucked into the source of vacuum 234.

The external fluid conduit 236 and the external waste conduit 240 may fluidly connect the disimpaction fluid reservoir 224 to the disimpaction fluid inlet of the device 200 and may fluidly connect the waste vacuum reservoir 232 to the waste vacuum outlet of the device 200 respectively, and may be made of a flexible material. The body portion of the irrigation device 200 may still be configured to be small and handheld, and with the reservoirs 224, 232 being outside of the body portion of the device it can be seen that the device 200 can be configured to be even smaller than the previous device 100. The external fluid conduit 236 and external waste conduit 240 may therefore be made to be flexible, bendable, stretchable, and/or compressible so that the irrigation device can be moved around and aimed as desired without interrupting any fluid connections. The external conduits 236, 240 may be detached and reattached from the device 200 and the reservoirs 224, 232 as desired, allowing for the disimpacted feces 106 in the waste vacuum reservoir 232 to be disposed of properly, the disimpaction fluid 104 of the fluid reservoir 224 to be refilled, and the fluid conduits 126 and waste conduits 238 of the irrigation device 200 to be cleaned out when desired. The aforesaid macerators that may break up the disimpacted feces 106. while not present in this embodiment, may be anywhere along the pathway the disimpacted feces travel in this embodiment. Thus, it can be seen that macerators may positioned anywhere in and along the waste conduits 238, the external waste conduit 240, and the waste vacuum reservoir 232 such that the macerators may break up the disimpacted feces 106 that may be present therein and/or travel therein.

The irrigation device 200 may be suitable for use in a treatment facility such as a hospital. In this case, the source of vacuum 234 may be a wall suction vacuum unit found in hospital rooms. After setting up the irrigation device 200, the doctor, nurse, or whoever may be operating the device 200 may hold the device 200 for a patient who may be laying down on an operating room bed positioned to allow for the operator to aim the irrigation device 200 to properly disimpact and treat the impacted feces of the patient. This embodiment of the irrigation device 200 need not be limited to hospital applications, and as such this irrigation device 200 may be configured to be used as a household treatment device as well.

Figure 8A:
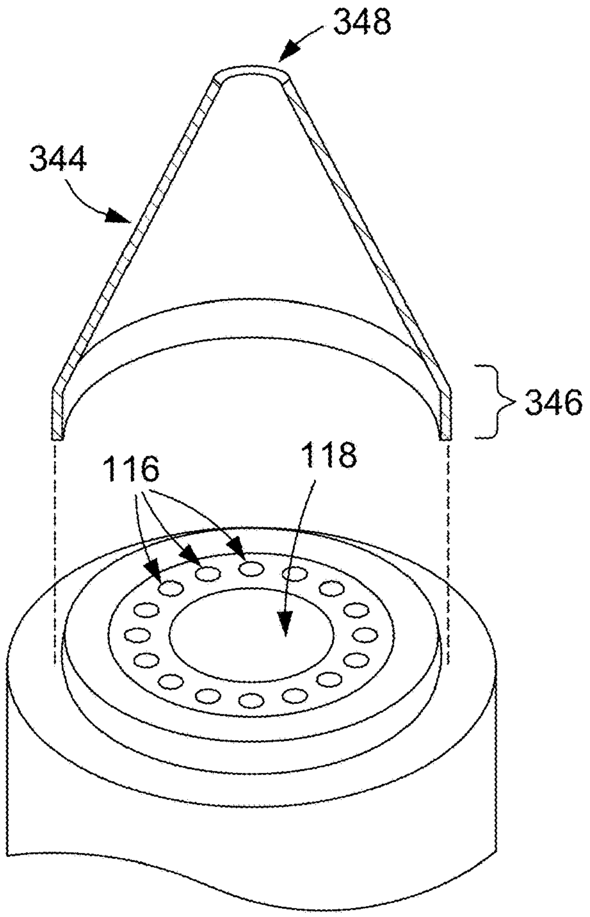
FIG. 8A is a cone attachment being attached to the first embodiment of the irrigation device.
Figure 8B:
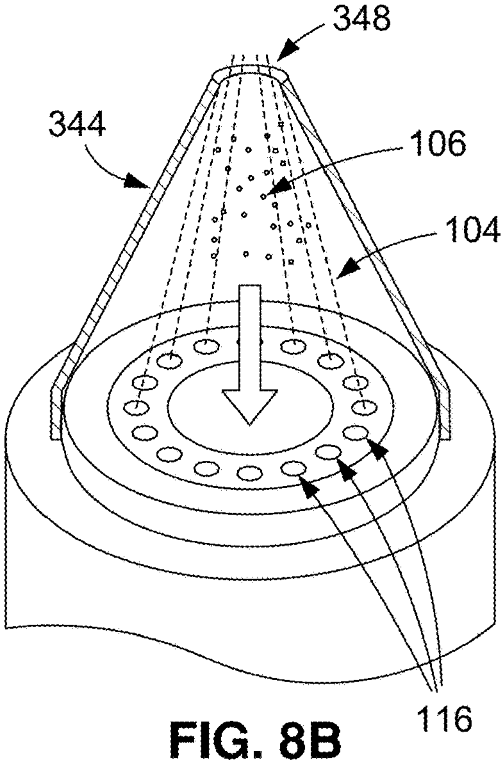
FIG. 8B is the first embodiment of the irrigation device being operated with the cone attachment attached to the same irrigation device.

Turning our attention now to FIGS. 8A and 8B, an exemplary cone attachment to the irrigation device is depicted, with FIG. 8A showing the cone attachment being attached to the first embodiment of the irrigation device and FIG. 8B showing the first embodiment of the irrigation device being operated with the cone attachment on. The cone attachment 344 may be shaped in several different configurations, but in the illustrated exemplary embodiment of the cone attachment 344, it is in a smooth conical shape. An attachment region 346 on one end of the cone attachment 344 may permit the cone attachment 344 to be attached on the distal portion 108 of the irrigation device 100. The attachment region 346 may allow a user/patient/operator to attach and detach the cone attachment 344 to the distal portion 108 of the irrigation device 100 as desired. The cone attachment 344 may also comprise a cone opening defining a cone aperture 348 through which the disimpaction fluid 104 may be further emitted through before disimpacting and/or treating the impacted feces. The cone attachment 344 may serve to catch overflow and/or act as a splash guard for the disimpaction fluid 104 being emitted, as well as to focus the disimpaction fluid 104 and suction of the source of vacuum 134 to particular impacted feces or regions of the anus. The outer surface of this cone attachment 344 may comprise the previously mentioned soft material, lubricant, and/or pressure sensors operative to notify the user if the device 100 is in position. A source of vacuum 134 may be operative to suck in the disimpacted feces 106 such that the disimpacted feces 106 is received by the cone aperture 348 before being received by the waste vacuum inlet.

Figure 9:
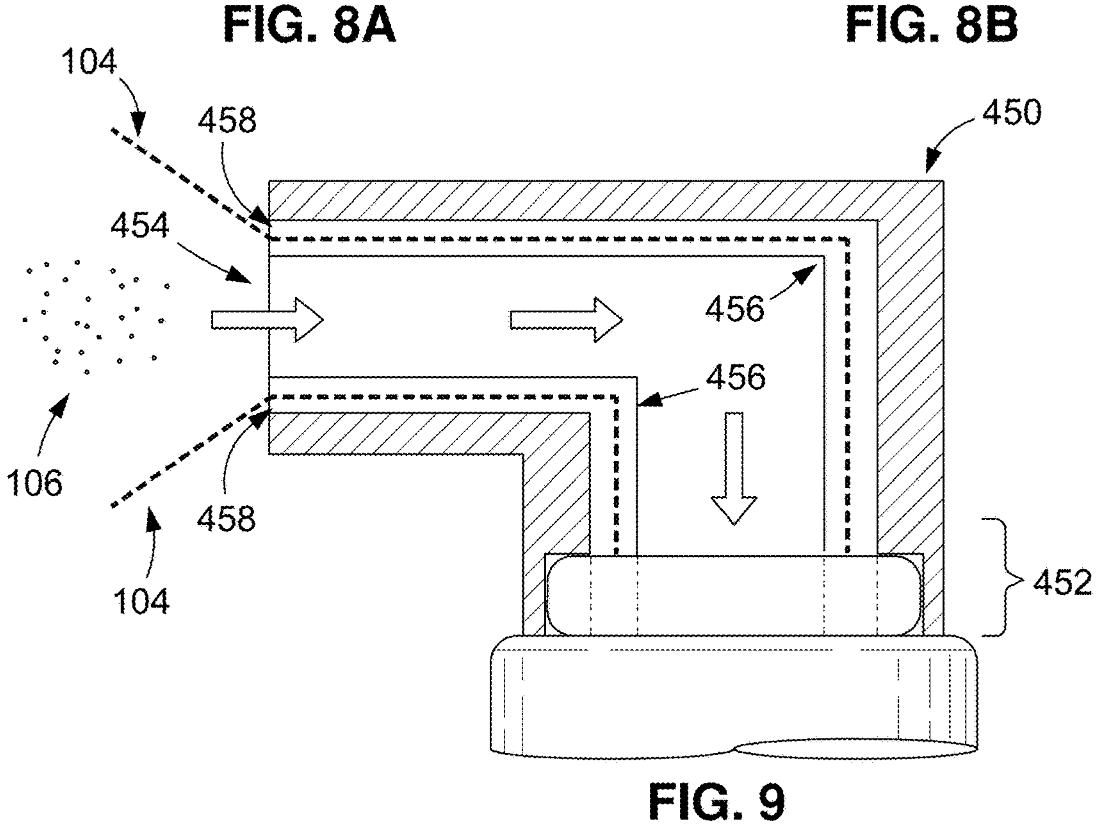
FIG. 9 is a close-up cross-sectional view of an angle attachment attached to the first embodiment of the irrigation device.

Turning to FIG. 9, a close-up cross-sectional view of an angle attachment attached to the first exemplary embodiment of the irrigation device 100 is depicted. The angle attachment 450, like the attachment region 346 of the cone attachment 344, may have an angle attachment region 452 to attach the angle attachment 450 to the distal portion 108 of the irrigation device 100. The angle attachment region 452 may allow a user to attach and detach the angle attachment 450 to the distal portion 108 of the irrigation device 100 as desired. The angle attachment 450 may comprise an angle opening defining an angle inlet aperture 454 that may receive disimpacted feces 106, which may then be subsequently received by the waste vacuum inlet. A source of vacuum 134 may be operative to suck in waste through the angle inlet aperture 454 and through the inlet aperture 118 of the waste vacuum inlet, and into a waste reservoir. The angle attachment 450 may further comprise angle fluid conduits 456 fluidly connected to the outlet apertures 116 and additionally fluidly connected to angle outlet apertures 458. It can be seen that the outlet apertures 116 may emit disimpaction fluid 104 into the angle fluid conduits 456. The disimpacted fluid 104 may then travel through the angle fluid conduits 456 such that the angle outlet apertures 458 may emit disimpaction fluid 104 towards the anus of the user/patient. The number, size, and configuration of the angle inlet apertures 454, the angle outlet apertures 458, and angle fluid conduits 456 may be modified and changed as desired, similar to the aforementioned inlet apertures 118, outlet apertures 116, 120, 122, and fluid conduits 126. The angle attachment 450, while not shown in this figure, may also comprise the aforementioned one or more macerators to break down disimpacted feces 106.

The angle attachment 450 may be configurable to enable the disimpaction fluid 104 to be emitted from the angle outlet apertures 458 according to one or more predefined jet configurations which themselves comprise the selection of a value of at least one adjustable parameter. As such, one may mechanically interact with the angle attachment 450 and/or activate the angle attachment 450 in one form or another to change adjustable parameters, such as the previously listed disimpaction fluid velocity, disimpaction fluid flow rate, and disimpaction fluid jet cone angle. Therefore, the angle attachment 450 serves mainly to redirect the flow of the disimpaction fluid to another direction and does not significantly limit the functions of the irrigation device 100 in comparison to when the angle attachment 450 is not attached to the distal portion 108 of the device. The angle attachment 450 may find utility in that one may hold the irrigation device 100 at a steep angle between their legs and have the angle attachment make the 90-degree turn needed into order to disimpact and/or treat the impacted feces. This may find applicability when a patient/user is on a bedpan or otherwise on their back. The angle of the angle attachment 450 shown in FIG. 9 is at a 90-degree angle, but angle attachments at an angle less than 90 degrees or greater than 90 degrees may also be used. Angle attachments may also have multiple angles within or have smooth curves as opposed to sharp angles. The angle attachment 450 may also be configured such that the attachment region 346 of the cone attachment 344 may be attached and detached as desired to the angle opening of the angle attachment 450 to give similar benefits as mentioned above in the discussion of the cone attachment 344.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments. Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. An irrigation device for treatment of fecal impaction in a patient, the irrigation device comprising:

a body portion comprising a disimpaction fluid inlet and a waste vacuum outlet, the body portion further comprising a distal portion configured for placement at and alignment with the anus of a patient, the distal portion comprising a disimpaction fluid outlet and a waste vacuum inlet, the disimpaction fluid outlet comprising one or more outlet apertures arranged to define an annulus, each outlet aperture being configured to emit a jet of disimpaction fluid, the waste vacuum inlet comprising one or more inlet apertures positioned internal to the annulus defined by the disimpaction fluid outlet;

wherein the disimpaction fluid inlet is configured to fluidly connect to a disimpaction fluid reservoir contained within the body portion for receiving a supply of disimpaction fluid;

wherein the waste vacuum outlet is configured to fluidly connect to a waste vacuum reservoir contained within the body portion for supplying a source of vacuum and for receiving waste;

wherein when the distal portion is placed at and aligned with the anus of a patient, the disimpaction fluid outlet is operative to emit a generally annular jet of disimpaction fluid into the anus of the patient so as to disimpact impacted feces, and the waste vacuum inlet is configured to receive and remove disimpacted feces;

wherein the device is configurable to enable the disimpaction fluid outlet to emit a generally annular jet of disimpaction fluid according to two or more predefined jet configurations;

wherein the two or more predefined jet configurations comprise the selection of a value for at least one adjustable parameter, the at least one adjustable parameter including a disimpaction fluid jet cone angle, the disimpaction fluid jet cone angle corresponding to alternative jet configurations between at least two of the two or more predefined jet configurations;

wherein the disimpaction fluid outlet is configured to emit heated disimpaction fluid; and wherein the body portion is sized and configured to be manually held in one hand of an operator when in operation.

2. The irrigation device of claim 1, wherein the disimpaction fluid is selected from the group consisting of: water, an intravenous fluid, a crystalloid solution, a colloidal solution, a buffer solution, a gas, or combinations thereof.

3. The irrigation device of claim 1, wherein the disimpaction fluid outlet comprises a plurality of individual outlet apertures arranged in an annular configuration, the plurality of individual outlet apertures being configured to collectively emit a generally annular jet of disimpaction fluid.

4. The irrigation device of claim 1, wherein the disimpaction fluid outlet comprises a single annular outlet aperture configured to emit a generally annular jet of disimpaction fluid.

5. The irrigation device of claim 1, wherein the disimpaction fluid outlet is configured to emit heated disimpaction fluid via the body portion further comprising a heating element for heating disimpaction fluid supplied by a disimpaction fluid reservoir.

6. The irrigation device of claim 1, wherein the disimpaction fluid outlet is configured to emit heated disimpaction fluid via the body portion being configured to receive disimpaction fluid that is heated prior to the disimpaction fluid being received at the disimpaction fluid inlet.

7. The irrigation device of claim 1, wherein the body portion further comprises one or more pumps for pumping disimpaction fluid through one or more conduits within the body portion.

8. The irrigation device of claim 1, wherein the at least one adjustable parameter further includes: disimpaction fluid velocity, disimpaction fluid flow rate, disimpaction fluid temperature, or combinations thereof.

9. A method for treating fecal impaction in a patient, the method comprising:

providing an irrigation device comprising a body portion sized and configured to be manually held in one hand of an operator when in operation, the body portion comprising a disimpaction fluid inlet, a waste vacuum outlet, and a distal portion configured for placement at and alignment with the anus of a patient, the distal portion comprising a disimpaction fluid outlet and a waste vacuum inlet, the disimpaction fluid outlet comprising one or more outlet apertures arranged to define an annulus, each outlet aperture being configured to emit a jet of disimpaction fluid, the waste vacuum inlet comprising one or more inlet apertures positioned internal to the annulus defined by the disimpaction fluid outlet;

fluidly connecting the disimpaction fluid inlet to a disimpaction fluid reservoir contained within the body portion for receiving a supply of disimpaction fluid;

fluidly connecting the waste vacuum outlet to a waste vacuum reservoir contained within the body portion for supplying a source of vacuum and for receiving waste; and placing the distal portion at and in alignment with the anus of a patient such that the irrigation device is not inserted into the anus of the patient, and actuating the irrigation device in order to cause the disimpaction fluid outlet to emit a generally annular jet of disimpaction fluid into the anus of the patient so as to disimpact impacted feces, with the disimpaced feces being received by and removed from the patient via the waste vacuum inlet.

10. The method of claim 9, wherein the disimpaction fluid is selected from the group consisting of: water, an intravenous fluid, a crystalloid solution, a colloidal solution, a buffer solution, a gas, or combinations thereof.

11. The method of claim 9, wherein the disimpaction fluid outlet comprises a plurality of individual outlet apertures arranged in an annular configuration, the plurality of individual outlet apertures being configured to collectively emit a generally annular jet of disimpaction fluid.

12. The method of claim 9, wherein the disimpaction fluid outlet comprises a single annular outlet aperture configured to emit a generally annular jet of disimpaction fluid.

13. The method of claim 9, wherein the disimpaction fluid outlet is configured to emit heated disimpaction fluid via the body portion further comprising a heating element for heating disimpaction fluid supplied by a disimpaction fluid reservoir.

14. The method of claim 9, wherein the disimpaction fluid outlet is configured to emit heated disimpaction fluid via the body portion being configured to receive disimpaction fluid that is heated prior to the disimpaction fluid being received at the disimpaction fluid inlet.

15. The method of claim 9, wherein the body portion further comprises one or more pumps for pumping disimpaction fluid through one or more conduits within the body portion.

16. The method of claim 9, wherein the device is configurable to enable the disimpaction fluid outlet to emit a generally annular jet of disimpaction fluid according to one or more predefined jet configurations.

17. The method of claim 16, wherein the one or more predefined jet configurations comprise the selection of a value for at least one adjustable parameter, the at least one adjustable parameter being selected from: disimpaction fluid velocity, disimpaction fluid flow rate, disimpaction fluid temperature, disimpaction fluid jet cone angle, or combinations thereof.

* * * * *